United States Patent [19]

Fallick

[11] Patent Number: 5,256,140

[45] Date of Patent: Oct. 26, 1993

US005256140A

[54] COMPOSITION FOR LEVELLING SKIN

[75] Inventor: Harry Fallick, King of Prussia, Pa.

[73] Assignee: Fallien Cosmeceuticals, Ltd., King of Prussia, Pa.

[21] Appl. No.: 859,327

[22] Filed: Mar. 27, 1992

[51] Int. Cl.$^5$ .............................................. A61M 31/00
[52] U.S. Cl. ...................................... 604/51; 424/572;
424/574; 424/78.08; 514/801
[58] Field of Search ............... 514/520, 572, 574, 801,
514/21, 571; 422/127, 128; 424/574, 520, 78.08;
435/1; 604/290, 51

[56] References Cited

U.S. PATENT DOCUMENTS

| | | | |
|---|---|---|---|
| 3,194,737 | 7/1965 | Jacobi | 514/21 |
| 3,839,590 | 10/1974 | Battista | 514/801 |
| 3,876,775 | 4/1975 | Izaka et al. | 514/21 |
| 3,991,184 | 11/1976 | Kludas et al. | 514/801 |
| 4,511,653 | 4/1985 | Play et al. | 514/21 |
| 4,749,522 | 6/1988 | Kamorei | 424/574 |
| 4,886,786 | 12/1989 | Lindstrom et al. | 514/21 |
| 5,000,963 | 3/1991 | Hefton | 435/1 |
| 5,053,229 | 10/1991 | Hattori et al. | 424/574 |
| 5,118,512 | 6/1992 | O'Leary | 424/520 |

FOREIGN PATENT DOCUMENTS 1015962  1/1966  United Kingdom ................ 422/127

*Primary Examiner*—Peter F. Kulkosky
*Attorney, Agent, or Firm*—John Lezdey

[57] ABSTRACT

The invention provides a method for preparing an injectable skin extract for use in levelling skin having depressions. The method provides for the steps of excising skin from a patient, cooling the skin to make it brittle, pulverizing the brittle skin, extracting collagen from the pulverized skin with an acid solution, evaporating off the acid and then solubilizing the resulting powder to form an injectable.

20 Claims, No Drawings

COMPOSITION FOR LEVELLING SKIN

FIELD OF THE INVENTION

The present invention relates to compositions for levelling skin. More particularly, there is provided injectable compositions for eliminating or reducing facial wrinkles, improving scarred areas and aiding in cosmetic or plastic surgery utilizing the patient's own epidermis and/or dermis as a source of collagen.

BACKGROUND OF THE INVENTION

There have been various compositions which have been utilized in plastic or cosmetic surgery to eliminate or reduce facial wrinkles or to correct blemishes caused by indentations in the skin, (i.e. acne scars). One method has been to use liposuction to extract materials from fatty areas of the body and then to use the tissue derived from the extraction. Another method had been to employ an injection of collagen derived from animals to build up the areas. However, the animal collagen could be allergenic to some patients. Silicone gels which were utilized have recently been withdrawn because of instances of side effects being reported.

It would be desirable to use a patient's own body as a source for providing the materials utilized for cosmetic or plastic surgery.

Use of a patient's own body parts would eliminate the fear of viral infections from donors and the possibility of allergic reactions. However, the injection of autologous dermis (autoderm) can lead to inclusion cyst formation.

Collagen is a fibrous protein formed from three helices wrapped around each other. Collagen makes up about a third of the body's protein and forms a useful substrate for tissue growth.

Hyaluronic acid is a naturally occurring mucopolysaccharide found, for example, in synovial fluid, in vitreous humor, in blood vessel walls and umbilical cord, and in other connective tissues. The polysaccharide consists of alternating N-acetyl-D-glucosamine and D-glucuronic acid residues joined by alternating $\beta$ 1-4glucosaminidic bonds, so that the repeating unit is -(1→4)-$\beta$-D-GlcA-(1→3)-$\beta$-D-GlcNAc-. In water, hyaluronic acid dissolves to form a highly viscous fluid. The molecular weight of hyaluronic acid isolated from natural sources generally falls within the range of $5 \times 10^4$ up to $1 \times 10^7$ daltons.

As used herein the term hyaluronic acid includes any of its hyaluronate salts, including, for example, sodium hyaluronate (the sodium salt), potassium hyaluronate, magnesium hyaluronate, and calcium hyaluronate.

The article of Everton et al in *J. Cosm. Surgery*. Vol. 4, No. 1, 1987 entitled "Injectable Autologous Dermis (Autoderm) Its Application in Facial Cosmetic Surgery," which is herein incorporated by reference, discloses the use of morsellized autologous dermis as a filling agent to obliterate wrinkles and scars. However, the entire dermis is utilized after removal of the epidermis. This procedure has the drawback in that cysts may develop after a period of time.

SUMMARY OF THE INVENTION

The present invention provides a method for preparing an injectable skin extract for use in eliminating skin depressions in patients. According to the method, a portion of skin is excised from the patient to be treated. The skin is preferably cooled to a temperature whereby it has become brittle and capable of being pulverized. The pulverized skin is denatured and extracted by means of a weak acid solution. The extract solution which contains the denatured collagen, is separated from the solids and the liquid is removed by an evaporation process to obtain a water soluble powder. The powder may be stored and/or formed into an injectable composition using a conventional pharmaceutical solution.

Advantageously, the injectable composition of the invention is prepared with hyaluronic acid.

It is therefore an object of the invention to prepare an injectable skin extract which is free of foreign matter of either an infectious or reactive matter.

It is a further object to prepare an injectable composition for eliminating skin depressions which is non-allergenic.

It is a still further object of the invention to prepare a wrinkle removing injectable composition which is not cyst forming.

DESCRIPTION OF THE PREFERRED EMBODIMENT

The preferred method of making the injectable composition will now be described in more detail. As one skilled in the art will appreciate the composition of the invention can be made by using protocols that are within the method of the invention yet are different in particulars from those described here.

A portion of skin from a patient, generally about 1 cm, is removed from a donor site on the body. Suitable donor sites include the inner arm, inner thigh, posterior ear abdomen and hip/groin area. The skin is then pulverized. The methods of pulverization can include the step of cooling the skin to a temperature wherein it is brittle. Suitable temperatures are generally about $-10°$ F. but temperatures as low as $-100°$ F. can also be utilized. Suitable low temperatures can be achieved utilizing liquid nitrogen, alcohol with solid carbon dioxide, acetone with solid carbon dioxide, and the like. The low cooling permits the skin to be pulverized using standard procedures including mortar and pestle or cryogenic grinding and freeze drying such as with a freezer mill sold by Spex Industries, Inc. of Edison, N.J. under the trademark SPEX 6700 Freezer/Mill.

Alternatively, the excised skin can be pulverized by means of ultrasonic disruption. Pursuant to this method, an ultrasonic processor, such as sold under the trademark VIBRA CELL by Sonico and Materials, Inc. of Danbury Connecticut can be used. According to the procedure of ultrasonic disruption, an ultrasonic power supply (generator) converts 50/60H$_3$ line voltage to high frequency 20KH$_3$ (20,000 cycles per second) electrical energy is transmitted to a piezoelectric transducer within a converter, where it is changed to mechanical vibrations. The vibrations from the converter are intensified by a probe creating pressure waves in a liquid. This action forms millions of microscopic bubbles which expand during a negative pressure excursion, and implode violently during a positive excursion. It is this action, referred to as cavitation, which produces the powerful shearing action and causes the molecules in the liquid to become intensely agitated. Using a acid solution in the ultrasonic processor allows denaturization and extraction of the collagen to occur.

Any weak acid solution can be utilized wherein the pH is about 2 to 4 preferably about 2.5. Suitable acids which may be used for denaturization and extraction include, but are not limited to, hydrochloric acid, citric acid and formic acid.

The liquid extract containing the collagen can be separated by filtration or centrifugation. The liquid may be evaporated by conventional methods to obtain powdered collagen. A preferred method of evaporation is freeze drying.

The powder which is obtained after the evaporation step can be stored or immediately formed into an injectable composition.

Usually about 1 ml of carrier liquid is used to solubilize the collagen containing powder. As a carrier there may be used water, saline solution, plasma or hyaluronic acid. Hyaluronic acid is advantageous in that it promotes new collagen, cell growth and binding. There is also slow resorb so that the degree of depression filling can be placed more accurately calculated.

The composition can be in a syringe, for example, a standard tuberculin syringe using a fine 28-gauge needle, and injected into facial wrinkles, folds, acne scars, and the like.

The collagen can be preserved for long periods of time utilizing a cryogenic preservation system such as the CRYOPLUS storage system of Cryomed, New Baltimore, MI.

Obviously, many modifications and variations of the invention, as herein above set forth, can be made without departing from the spirit and scope thereof, and therefore only such limitations should be imposed as are indicated in the appended claims.

What is claimed is:

1. A method for the injection and preparation of an injectable skin extract for a human patient which comprises the steps of:
   A. excising a portion of skin from the patient to receive the extract;
   B. pulverizing said skin;
   C. denaturing and extracting said pulverized skin with an acid solution so as to obtain denatured collagen;
   D. evaporating the acid solution from said extract containing denatured collagen so as to obtain a powder, and then,
   E. solubilizing said powdered extract to form an injectable solution, whereby after injection the extract causes levelling of the skin where injected.

2. The method of claim 1 wherein said skin cooled to a temperature whereby it becomes brittle prior to pulverizing.

3. The method of claim 2 wherein said skin is cooled to at least −10° F.

4. The method of claim 3 wherein said skin in step B is cooled with liquid nitrogen.

5. The method of claim 1 wherein said skin in step C is extracted with an acid at a pH of about 2 to 4.

6. The method of claim 1 wherein said acid is selected from the group consisting of hydrochloric acid, citric acid and formic acid.

7. The method of claim 1 wherein said skin from step A is subjected to ultrasonic disruption.

8. The method of claim 7 wherein the ultrasonic disruption is in an acid medium.

9. The method of claim 1 wherein said powdered extract is solubilized with water or saline solution.

10. The method of claim 1 wherein said powered extract is solubilized with plasma.

11. The method of claim 1 wherein said powdered extract is solubilized with hyaluronic acid.

12. An injectable solution for levelling skin depressions prepared by the process of claim 1.

13. An injectable solution for levelling skin depressions prepared by the process of claim 2.

14. An injectable solution for levelling skin depressions prepared by the process of claim 3.

15. An injectable solution for levelling skin depressions prepared by the process of claim 5.

16. An injectable solution for levelling skin depressions prepared by the process of claim 6.

17. An injectable solution for levelling skin depressions prepared by the process of claim 7.

18. An injectable solution for levelling skin depressions prepared by the process of claim 9.

19. An injectable solution for levelling skin depressions prepared by the process of claim 10.

20. An injectable solution for levelling skin depressions prepared by the process of claim 11.

* * * * *